United States Patent
Bryant

(10) Patent No.: US 6,423,061 B1
(45) Date of Patent: Jul. 23, 2002

(54) HIGH TIBIAL OSTEOTOMY METHOD AND APPARATUS

(75) Inventor: Richard M. Bryant, Clemmons, NC (US)

(73) Assignee: AMEI Technologies Inc., Wilmington, DE (US)

(*) Notice: Subject to any disclaimer, the term of this patent is extended or adjusted under 35 U.S.C. 154(b) by 0 days.

(21) Appl. No.: 09/525,992

(22) Filed: Mar. 14, 2000

(51) Int. Cl.[7] ............................................. A61B 17/00
(52) U.S. Cl. .......................................... 606/57; 606/54
(58) Field of Search ............................. 606/53–55, 57, 606/58, 60

(56) References Cited

U.S. PATENT DOCUMENTS

| | | | |
|---|---|---|---|
| 3,604,414 A | 9/1971 | Borges | 128/92 D |
| 3,783,880 A | 1/1974 | Kraus | 128/82.1 |
| 3,918,440 A | 11/1975 | Kraus | 128/82.1 |
| 4,102,339 A | 7/1978 | Weber et al. | 128/92 E |
| 4,312,336 A | 1/1982 | Danieletto et al. | 128/92 A |
| 4,488,542 A | * 12/1984 | Helland | 606/59 |
| RE31,809 E | 1/1985 | Danieletto et al. | 128/92 A |
| 4,549,547 A | 10/1985 | Brighton et al. | 128/419 F |
| 4,604,997 A | 8/1986 | DeBastiani et al. | 128/92 A |
| 4,620,543 A | 11/1986 | Heppenstall et al. | 128/419 F |
| 4,621,627 A | 11/1986 | DeBastiani et al. | 128/92 ZZ |
| 4,628,919 A | * 12/1986 | Clyburn | 606/55 |
| 4,793,325 A | 12/1988 | Cadossi et al. | 600/14 |
| 4,828,277 A | 5/1989 | DeBastiani et al. | 279/1 SG |
| 4,887,111 A | 12/1989 | Ben-Dov | 128/419 F |
| 4,889,111 A | 12/1989 | Ben-Dov | 128/419 |
| 4,946,179 A | 8/1990 | DeBastiani et al. | 279/1 SG |
| 4,957,496 A | 9/1990 | Schmidt | 606/70 |
| 4,978,347 A | 12/1990 | Ilizaarov | 606/54 |
| 4,988,349 A | 1/1991 | Penning | 606/58 |
| 5,019,077 A | 5/1991 | DeBastiani et al. | 606/54 |
| 5,026,374 A | 6/1991 | Dezza et al. | 606/72 |
| 5,056,518 A | 10/1991 | Pethica et al. | 128/419 F |
| 5,062,844 A | 11/1991 | Jamison et al. | 606/54 |
| 5,067,954 A | 11/1991 | Ilizarov | 606/58 |
| 5,129,903 A | 7/1992 | Luhr et al. | 606/71 |
| 5,209,750 A | 5/1993 | Stef | 606/54 |
| 5,281,224 A | 1/1994 | Faccioli et al. | 606/62 |
| 5,292,322 A | 3/1994 | Faccioli et al. | 606/59 |
| 5,304,180 A | 4/1994 | Slocum | 606/69 |
| 5,314,401 A | 5/1994 | Tepper | 600/14 |
| 5,320,622 A | 6/1994 | Faccioli et al. | 606/58 |
| 5,320,623 A | 6/1994 | Pennig | 606/59 |
| 5,330,477 A | 7/1994 | Crook | 606/69 |
| 5,342,360 A | 8/1994 | Faccioli et al. | 606/56 |
| 5,358,504 A | 10/1994 | Paley et al. | 606/56 |
| 5,376,090 A | 12/1994 | Pennig | 606/54 |
| 5,413,596 A | 5/1995 | Kronberg | 607/51 |

(List continued on next page.)

FOREIGN PATENT DOCUMENTS

SU   1271-528 A   11/1986

OTHER PUBLICATIONS

PCT Search Report PCT/US00/35527, May 4, 2001.
"Orthopedic Fixation Devices," Richard M. Slone, M..D., et al., RadioGraphics, vol. II, #5, pp. 823–847, 1991.
"Medial Compartment Osteoarthritis" Brochure, Orthofix, Jan. 1998.

Primary Examiner—Jeffrey A. Smith
Assistant Examiner—Michael B. Priddy
(74) Attorney, Agent, or Firm—Baker Botts L.L.P.

(57) ABSTRACT

External fixation apparatus and method are disclosed for use in osteotomy and other medical procedures. The apparatus includes a stabilizing portion adapted to be externally coupled to an anterior portion of a tibial bone. The apparatus also includes a angulation portion adapted to be externally coupled to another anterior portion of the tibial bone and coupled to the stabilizing portion. The angulation portion may be selectively adjustable to angulate a portion of the tibial bone about an axis of rotation offset from a longitudinal axis of the tibial bone following an osteotomical procedure on the tibial bone.

12 Claims, 4 Drawing Sheets

U.S. PATENT DOCUMENTS

| | | |
|---|---|---|
| RE34,985 E | 6/1995 | Pennig .................. 606/58 |
| 5,433,720 A | 7/1995 | Faccioli et al. ............. 606/87 |
| D361,555 S | 8/1995 | Erickson et al. ........... D14/114 |
| 5,437,667 A * | 8/1995 | Papierski et al. ........... 606/55 |
| 5,441,527 A | 8/1995 | Erickson et al. ............. 607/51 |
| 5,443,464 A | 8/1995 | Russell et al. ............. 606/54 |
| 5,458,558 A | 10/1995 | Liboff et sl. .................. 600/13 |
| 5,458,627 A | 10/1995 | Baranowski, Jr. et al. .... 607/51 |
| RE35,129 E | 12/1995 | Pethica et al. ............... 607/2 |
| D367,529 S | 2/1996 | Price et al. ................. D24/127 |
| D367,531 S | 2/1996 | Price et al. ................. D24/143 |
| 5,496,319 A | 3/1996 | Allard et al. ................ 606/56 |
| 5,524,624 A | 6/1996 | Tepper et al. .......... 128/660.03 |
| 5,545,162 A * | 8/1996 | Huebner ..................... 606/57 |
| D373,632 S | 9/1996 | Price et al. ................. D24/127 |
| D373,635 S | 9/1996 | Price et al. ................. D24/140 |
| 5,558,654 A | 9/1996 | Hardy ........................ 604/322 |
| 5,565,005 A | 10/1996 | Erickson et al. ............. 607/51 |
| 5,591,164 A | 1/1997 | Nazre et al. ................. 606/59 |
| 5,601,551 A | 2/1997 | Taylor et al. ................. 606/54 |
| 5,620,449 A | 4/1997 | Faccioli et al. ............. 606/98 |
| 5,653,707 A | 8/1997 | Taylor et al. ................. 606/54 |
| 5,662,648 A | 9/1997 | Faccioli et al. ............. 606/54 |
| 5,662,650 A | 9/1997 | Bailey et al. ................. 606/59 |
| 5,681,313 A | 10/1997 | Diez .......................... 606/69 |
| 5,681,318 A | 10/1997 | Pennig et al. ................. 606/98 |
| 5,688,271 A | 11/1997 | Faccioli et al. ............. 606/54 |
| 5,702,389 A | 12/1997 | Taylor et al. ................. 606/54 |
| 5,707,370 A | 1/1998 | Berki et al. ................. 606/59 |
| 5,728,095 A | 3/1998 | Taylor et al. ................. 606/54 |
| 5,728,096 A | 3/1998 | Faccioli et al. ............. 606/54 |
| 5,743,898 A | 4/1998 | Bailey et al. ................. 606/54 |
| 5,766,179 A | 6/1998 | Faccioli et al. ............. 606/98 |
| 5,766,231 A | 6/1998 | Erickson et al. ............. 607/51 |
| 5,797,908 A | 8/1998 | Meyers et al. ................. 606/54 |
| 5,803,924 A * | 9/1998 | Oni et al. ..................... 606/54 |
| 5,827,282 A | 10/1998 | Pennig ........................ 606/54 |
| 5,827,283 A | 10/1998 | Groiso et al. ................. 606/57 |
| 5,827,286 A | 10/1998 | Incavo et al. ................. 606/71 |
| 5,855,580 A | 1/1999 | Kreidler et al. ............. 606/71 |
| 5,863,292 A * | 1/1999 | Tosic .......................... 606/56 |
| 5,891,143 A | 4/1999 | Taylor et al. ................. 606/56 |
| 5,893,850 A * | 4/1999 | Cachia ........................ 606/72 |
| 5,897,555 A * | 4/1999 | Clyburn et al. ............... 606/54 |
| 5,902,302 A | 5/1999 | Berki et al. ................. 606/59 |
| 5,902,304 A | 5/1999 | Walker et al. ................. 606/71 |
| 5,928,234 A * | 7/1999 | Manspeizer ................... 606/61 |
| 5,941,879 A | 8/1999 | Walulik et al. ............... 606/61 |
| 5,964,763 A * | 10/1999 | Incavo et al. ................. 606/71 |
| 5,997,490 A | 12/1999 | McLeod et al. ............. 601/97 |
| 6,187,005 B1 * | 2/2001 | Brace et al. .................. 606/61 |
| 6,203,548 B1 * | 3/2001 | Helland ...................... 606/105 |
| 6,235,029 B1 * | 5/2001 | Faccioli et al. ............. 606/54 |
| 6,328,737 B1 * | 12/2001 | Moorcroft et al. ............ 606/57 |

* cited by examiner

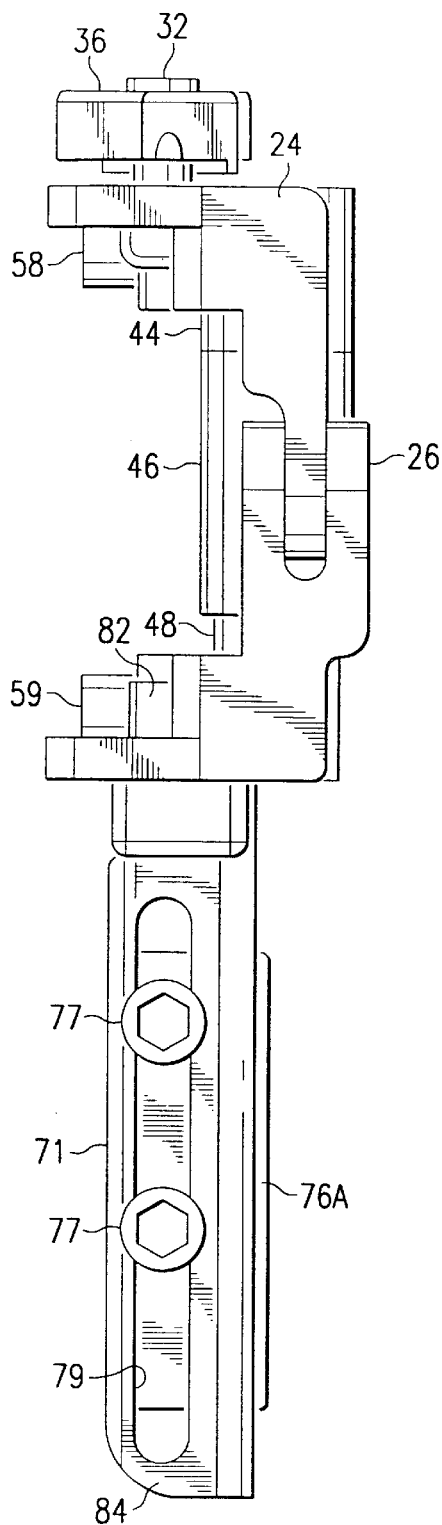
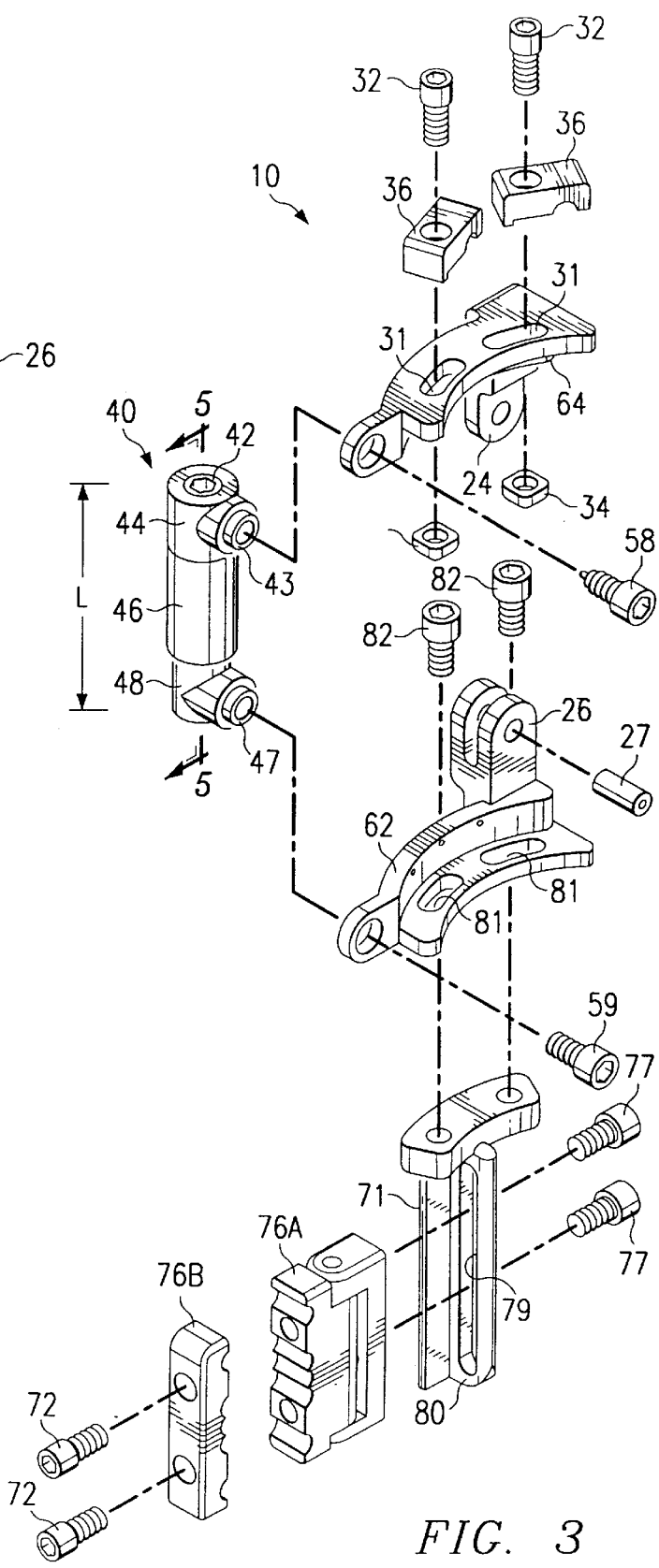
FIG. 2
FIG. 3

HIGH TIBIAL OSTEOTOMY METHOD AND APPARATUS

BACKGROUND OF THE INVENTION

Procedures such as limb lengthening used to address congenital or traumatic conditions may include an orthopedic osteotomical procedure such as a high tibial osteotomy (HTO). For example, an HTO procedure may be used to treat patients who suffer from a variety of ailments including varus or valgus deformities; that is, abnormal positions of a bone of the leg or foot. This procedure may be used to adjust cartilage wear patterns and/or the distribution of stress along the tibial and knee areas. Performing valgus or varus correction typically adjusts the angulation of a tibial bone and may, in many cases, delay or eliminate the need to replace a joint such as the knee.

Proper adjustment of limb angulation desirably includes adjustment of the bone while the bone is healing. External stabilization or fixation devices are often used to compress and properly align an osteotomy during the healing process. Multiple bone screws, wires and/or pins are often used to provide compression or to attach an external fixation device which provides compression, prevents displacement of bone or tissue fragments, and supports the bone or tissue fragments during healing. These screws, wires and/or pins may be placed through one or both cortices of bone to properly position and align the osteotomy.

Some conventional fixation devices may be used to adjustably secure a first bone portion above an osteotomy in a position relative to a second bone portion below the osteotomy. Unfortunately, some of these devices may require physician intervention for adjustment, and/or may not allow functional use of the recovering limb while the limb is healing. For example, these devices may impair a patient's ability to walk. Furthermore, many of these devices may impair a physician's ability to monitor the healing process and/or access the area surrounding the osteotomy. For example, some conventional fixation devices may block or limit radiographic, ultrasonic and/or visual examination of a treatment site.

In addition, some of these devices include a center of rotation that is generally aligned with a center of the tibia. These devices may require additional time for a separate distraction of the bone before the angulation adjustment process may begin, which may result in an extended treatment period. Moreover, these devices may in some cases be used to angulate a tibia with an osteotomy that is not aligned with an adjustment angle of the fixation device. Such misalignment may not provide an optimal level of angulation and/or control thereof.

SUMMARY OF THE INVENTION

From the foregoing, it may be appreciated that a need has arisen for providing an improved high tibial osteotomy device. In accordance with the teachings of the present invention, an apparatus and method are provided that substantially reduce. or eliminate disadvantages and problems of conventional external fixation devices.

One aspect of the present invention is represented by a high tibial osteotomy apparatus. The apparatus preferably includes a stabilizing portion adapted to be externally coupled to an anterior portion of a tibial bone. The apparatus may also include an angulation portion adapted to be externally coupled to another anterior portion of the tibial bone and coupled to the stabilizing portion. The angulation portion may be selectively adjustable to angulate a portion of the tibial bone about a center of rotation offset from a center of the tibial bone following an osteotomical procedure on the tibial bone.

Another aspect of the present invention includes an osteotomy guide for placement of an osteotomy. The osteotomy guide has a generally rigid member adapted to be releasably coupled to an external fixation device. The osteotomy guide may also include a receptacle disposed in the member. The receptacle is preferably adapted to receive a plurality of instruments to be used in an osteotomical procedure on a tibial bone.

The present invention provides several important advantages. Various embodiments of the invention may have none, some, or all of these advantages. The invention may permit a variety of monitoring activities. For example, the invention includes a window that allows access and/or visual inspection of the osteotomy. In some applications, the window may include materials that do not obstruct one or more imaging wavelengths. For example, the window may include radiolucent material that is relatively transparent to x-rays. The invention may be secured to an anterior portion of a tibial bone, permitting functional use of the recovering limb while the limb is healing. The invention includes an center of rotation offset from a center of the tibial bone. Such an advantage may reduce or eliminate the need for a separate distraction period to avoid bone impingement before beginning the process of angulation adjustment. For example, the invention may eliminate the need to wait for lengthening to be performed before angulation commences. That is, angulation may commence without waiting the approximately seven to ten days typically required for a separate lengthening or distraction period.

The invention may also allow improved control over conventional methods. For example, the invention allows a patient to perform incremental angulation adjustments. These incremental adjustments desirably promote angulation while reducing the risk of consolidation or solidification of the bone. Such an advantage also may reduce the overall treatment time and/or improve the control in angulation.

The invention may also permit adjustments to be performed so that an osteotomy may be properly compressed. The invention also provides for flexibility in pin placement. The invention may also be used for treatment for both a patient's left and the right limbs.

The invention may also provide guidance to a physician in performing an osteotomy. For example, the invention may allow proper alignment of the osteotomy with a center of rotation. Such an advantage may improve the control and accuracy of the angulation adjustment process.

BRIEF DESCRIPTION OF THE DRAWINGS

For a more complete understanding of the present invention, and the advantages thereof, reference is now made to the following written description taken in conjunction with the accompanying drawings, in which:

FIG. 2 is a side view of a high tibial osteotomy device incorporating teachings of the present invention;

FIG. 3 is a schematic drawing showing another isometric view of a high tibial osteotomy device incorporating teachings of the present invention;

DETAILED DESCRIPTION OF THE INVENTION

Preferred embodiments of the present invention and its advantages are best understood by referring to the FIGS. 1–8 of the drawings, like numerals being used for like and corresponding parts of the various drawings.

One embodiment for an HTO device 10 incorporating various features of the present invention is discussed in detail in conjunction with FIGS. 1–5. HTO device 10 may be used in the performance and/or in the treatment of high tibial osteotomical procedures. HTO device 10 is operable to attach to an anterior portion of tibia 122 of a patient and, in some applications, a physician may perform the osteotomy after HTO device 10 is attached to tibia 122. A physician may also use an osteotomy guide to perform the osteotomy. One embodiment of an osteotomy guide incorporating various features of the present invention is discussed in detail in conjunction with FIGS. 6–8.

Figure 1:
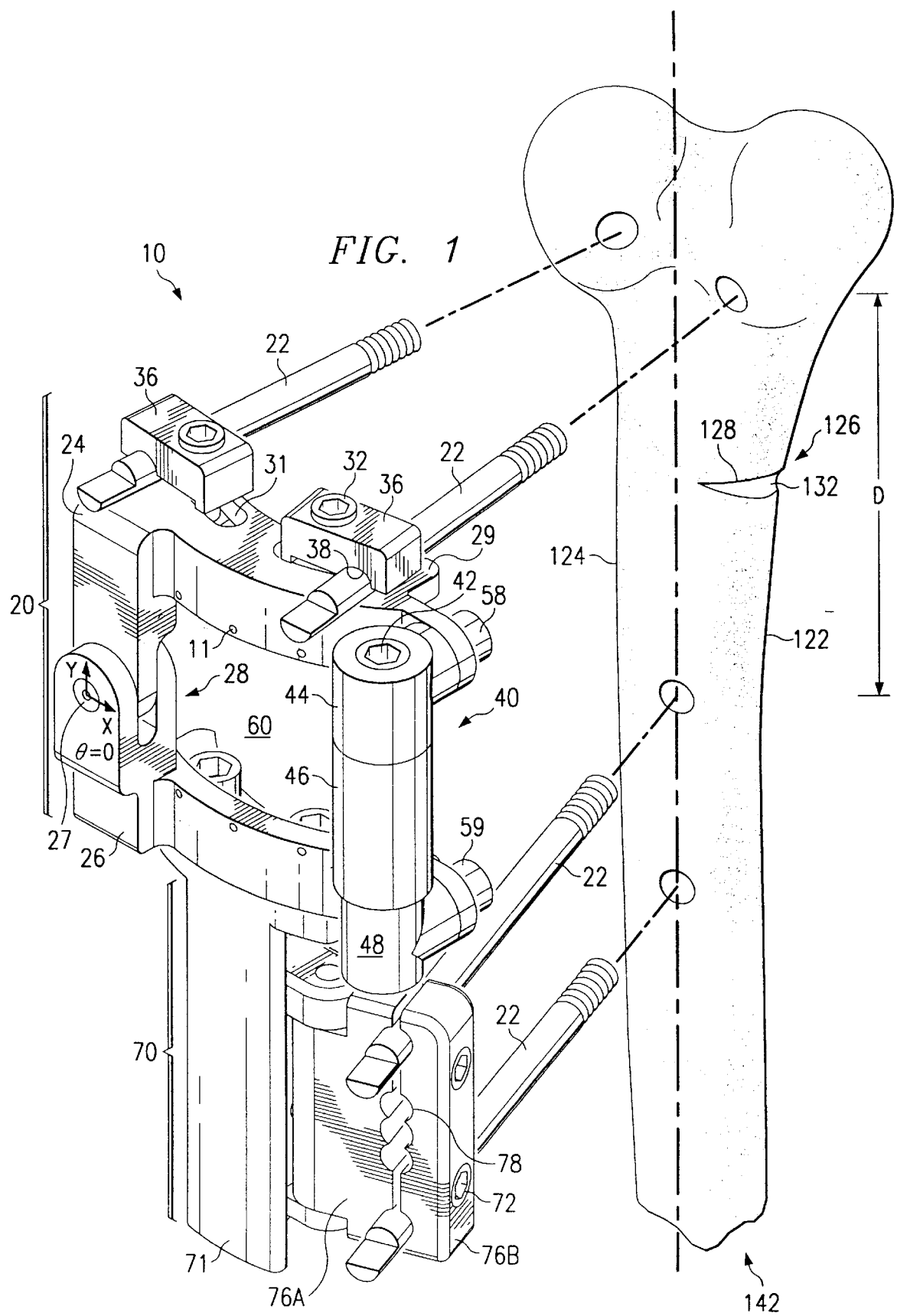
FIG. 1 is a schematic drawing showing an isometric view of a high tibial osteotomy device incorporating teachings of the present invention.

HTO device 10 may be used to control the adjustment in angulation to tibia 122 about a center or axis of rotation offset from longitudinal axis or longitudinal centerline 142 of tibia 122. FIG. 1 illustrates a tibia 122 that includes a generally transverse osteotomy 132 whose penetration through tibia 122 stops short of lateral cortex 124.

Satisfactory healing of the bone generally requires reduction and fixation of osteotomy 132. For example, immediately after an osteotomical procedure, the osteotomy surfaces are preferably disposed adjacent to each other, and compression preferably provided at the osteotomy site to increase the area of contact between the osteotomy surfaces. Ideally, flexibility in placement and adjustment of fixation devices may improve control of the compression process. In this embodiment, HTO device 10 may be attached to tibia 122 by means of stabilizing devices or pins 22. HTO device 10 is disposed substantially externally to the body of the patient (not explicitly shown). Each pin 22 penetrates the body of the patient at a desired location and is connected to tibia 122. HTO device 10 may be attached to tibia 122 to both stabilize osteotomy 132 and permit control of angulation of tibia 122. In the embodiments illustrated in FIGS. 1 and 2, HTO device 10 is operable to control angulation of a medial portion 126 of tibia 122 while callus tissue 128 forms therein.

FIG. 1 is a schematic drawing showing an isometric view of a high tibial osteotomy device incorporating teachings of the present invention. HTO device 10 preferably includes an angulation portion 20 and a stabilizing portion 70. Angulation portion 20 may be used in conjunction with stabilizing portion 70 to apply gradual correction angulation means to and control final limb alignment of tibia 122.

By way of example and not by limitation, angulation portion 20 includes a proximally located first portion 24, and at least one clamp mechanism 36 that is releasably coupled thereto. HTO device 10 is shown with an adjustment angle θ of approximately zero degrees, where adjustment angle θ is formed in an x-y plane formed by a y axis through hinge 28 and relative to an x axis through hinge 28 generally parallel to surface 29 of first portion 24. Thus, HTO device 10 is operable to angulate tibia 122 about a center of rotation centered at hinge 28 that is offset from center 142 of tibia 122. Angulation portion 20 also comprises an adjustment portion 40 that is operable to adjustably couple first portion 24 to distally located second portion 26.

Adjustment portion 40 may be selectively adjusted to increase or decrease adjustment angle θ. This adjustment pivots about hinge 28 and results in expansion of medial portion 126 of tibia 122. By way of example and not by limitation, adjustment angle θ may be selectively expanded by rotating hex socket 42. One example of such an expansion of adjustment angle θ is illustrated and discussed in further detail in conjunction with FIG. 4. Adjustment portion 40 is disposed on an exterior side of angulation portion 20 relative to the patient in this embodiment. The invention also contemplates an adjustment portion 40 disposed interiorly (relative to the patient) to angulation portion 20.

Also by way of example and not by limitation, angulation portion 20 includes a second portion 26 that is hingedly coupled to first portion 24 by hinge 28. Hinge 28 may be implemented using a variety of methods. In this embodiment, hinge 28 may include a cylindrical pin 27 that rotatably couples cylindrically-shaped receptacles in both second portion 26 to first portion 24. The present invention also contemplates the use of other hingeable, pivotable or rotatable means to couple second portion 26 to first portion 24.

First portion 24, second portion 26, and adjustment portion 40 form and enclose a window 60. Window 60 provides an unobstructed view of tibial bone 122 that desirably allows examination of and/or access to osteotomy 132. For example, the physician and/or the patient may palpitate, visually inspect and/or monitor healing of the wound created by osteotomy 132 through window 60. In addition, window 60 permits an unobstructed view of osteotomy 132 and callus portion 128 for a variety of examination and monitoring procedures. Such an advantage allows a variety of examination techniques to be used to observe the healing processes of osteotomy 132 and/or valgus and/or varus correction of bone 122 during treatment. For example, procedures including, but not limited to, radiographic imaging (e.g., fluoroscopic, x-ray, magnetic resonance imaging, and computed tomography scanning techniques) and ultrasonic imaging may be used to capture unobstructed views of callus portion 128 at a variety of points during the healing process as tibial bone 122 is angulated.

In some applications, it may be desirable for some or all of the elements within angulation portion 20 to be manufactured using a variety of composite materials. For example, those elements forming and enclosing window 60 may include radiolucent materials that are transparent to radiographic wavelengths. Such an embodiment provides the advantage of a larger unobstructed imaging area through which a physician may obtain images to analyze the healing process. In this embodiment, stabilizing portion 70 includes a support member 71 that may be releasably coupled to second portion 26 as discussed in further detail in conjunction with FIGS. 2 and 3. In other applications, second portion 26 and stabilizing portion 70 may include a single integrated member. Stabilizing portion 70 also includes clamp mechanisms 76A and 76B. Clamp mechanism 76A may include one or more portions and may also be releasably coupled to support member 71 as discussed in conjunction with FIGS. 2 and 3.

HTO device 10 may be anteriorly mounted on tibia 122 by means of at least four pins 22 as shown in the embodiment illustrated in FIG. 1. Two proximal pins 22 are located above osteotomy 132, and two distal pins 22 are located below osteotomy 132 a distance D from proximal pins 22. The present invention contemplates the use of more or fewer pins. For example, in some applications it may be desirable to utilize three distal pins 22. The present invention also contemplates the use of other means of attaching HTO device 10 to tibia 122. For example, HTO device 10 may be connected to tibia 122 using stabilizing devices including, but not limited to, bone screws, wires, pins or a combination thereof. Pins 22 may be manufactured using any suitable implantable grade materials.

As illustrated in FIG. 1, proximal pins 22 are releasably secured within a slot or receptacle 38 formed within each of two clamp mechanisms 36. Also by way of example and not by limitation, stabilizing portion 70 includes at least one clamp mechanism operable to secure HTO device 10 to at least two distal pins 22. In this embodiment, stabilizing portion 70 includes clamp mechanisms 76A and 76B. Clamp mechanism 76B may be releasably secured to clamp mechanism 76A by adjusting cap screws 72. A plurality of slots or receptacles 78 may be formed when clamp mechanism 76A is coupled to clamp mechanism 76B. Receptacles 78 may be generally linearly aligned as illustrated, staggered in other configurations, and/or be disposed in either or both clamp mechanisms 76A and 76B. Distal pins 22 may be releasably secured within at least two receptacles 78.

A variety of methods may be used to selectably adjust the placement of pins 22 in, and pressure applied to, tibia 122. In this embodiment, each clamp mechanism 36 may be selectively positioned in a slot or track 31 disposed in surface 29. By way of example and not by limitation, each clamp mechanism 36 may be translated along first portion 24, and may be releasably fixed using cap screw 32. The present invention also contemplates the use of a single slot 31 in which both clamp mechanisms 36 may be positioned, or other mechanisms for adjusting placement of proximal pins 22. Each of these elements in angulation portion 20 may reside in a volume whose surface generally corresponds with a contour of a patient's lower leg. Such a configuration may be desirable in applications where placement of pins 22 may be selectively adjustable. Alignment and adjustment of distal pins 22 is discussed in conjunction with FIGS. 2 and 3.

In operation, a physician may first align and then stabilize HTO device 10 with respect to tibia 122 by inserting one or more K-wires (not explicitly shown) through receptacles 11 into tibia 122. In addition, the physician may also insert one or more K-wires through a receptacle in pin 27 into tibia 122. The physician may then accurately position proximal screws 22 and then distal screws 22. In some embodiments, the physician may also releasably couple an osteotomy guide 200 to HTO device 10. Osteotomy guide 200 may be used to assist the physician in performing the osteotomical procedure, and is discussed in further detail in conjunction with FIGS. 4–6.

FIG. 2 is a side view of a high tibial osteotomy device incorporating teachings of the present invention. Where osteotomy 132 is a medial osteotomy 132 on a right tibial bone 122, FIG. 2 illustrates a medial view of HTO device 10. In this embodiment, first portion 24 is rotatably coupled to a generally unshaped second portion 26 by hinge 28 (not explicitly shown). One of proximal pins 22 is secured by clamp mechanism 36. By way of example and not by limitation, cap screws 78 are positioned in a slot or track 79 on a side 84 of support member 71. Set screws 78 may be used to adjust and releasably couple clamp mechanism 76A to side 80 (not explicitly shown) of support member 71. Such adjustment may be used to position distal pins 22 in tibial bone 122 as desired. In this embodiment, this adjustment may be performed by adjusting and fixing the position of cap screws 78 in slot 79. Clamp mechanisms 76A and 76B are discussed in further detail in conjunction with FIG. 3.

HTO device 10 is positioned at a distance H from tibial bone 122 and substantially externally to the body of the patient (not explicitly shown). Distance H may vary as desired, and/or according to the length of proximal and distal pins 22. For example, distance H may sized to reduce the profile of HTO device 10, while remaining sized large enough for palpitating the wound created by osteotomy 132 in a region between HTO device 10 and the patient's body. Such an advantage provides an unobstructed view of tibial bone 122 from both a medial and a lateral view that, in addition to window 60, also desirably allows examination of and/or access to osteotomy 132. Such an advantage allows a variety of examination techniques to observe the healing processes of osteotomy 132 and/or valgus and/or varus correction of bone 122 during treatment, such as radiographic and sonic imaging.

FIG. 3 is a schematic drawing showing another isometric view of a high tibial osteotomy device incorporating teachings of the present invention. By way of example and not by limitation, clamp mechanism 76A is releasably coupled to side 80 of support member 71 by cap screws 78. In some applications, clamp mechanism 76A may alternatively be releasably coupled to side 84 of support member 71. Second portion 26 and first portion 24 also include surfaces 62 and 64, respectively.

Clamp mechanisms 36 may be selectively positioned in slot or track 31 by a variety of methods. In this embodiment, cap screws 32 may be tightened to a nut 34 that is larger than slot 31 to retain clamp mechanisms 36. Alternatively, other methods and devices may be used to tighten clamp mechanisms 36 to slot 31 including, but not limited to, bolts and threaded devices.

In this embodiment, distal pins 22 may be aligned and adjusted in at least two ways. First, a generally lateral position of stabilizing portion 70 with respect to angulation portion 20 may be adjusted in one or more slots 81 residing in second portion 26. For example, bolts 82 may be used to position and tighten support member 70 to slot 81. Second, the positions of distal pins 22 may also be adjusted to, for example, apply compression to osteotomy 132. For example, the distance D between proximal pins 22 and distal pins 22 may be selectively expanded or contracted in a length and a direction generally parallel to tibia 122. In this embodiment, this adjustment may be performed by adjusting the position of clamp mechanisms 76A and 76B in slot 79 and fixing the position thereof by using cap screws 78. The invention also contemplates a variety of other methods to releasably couple clamp mechanism 76A to stabilizing portion 70.

As hex socket 42 is rotated, the length L of adjustment portion 40 increases. Thus, adjustment portion 40 is desirably operable to rotatably couple to angulation portion 20 by using upper screw 58 and lower screw 59 to allow for such an increase. Upper screw 58 is operable to couple to a threaded boss portion 43 of upper cap 44, and lower screw 59 is operable to couple to a threaded boss portion 47 of body 48. Bosses 43 and 47 may desirably be inserted through receptacles (not explicitly shown) of first portion 24 and second portion 26, respectively. Such a configuration may distribute any load applied to adjustment portion 40, thus reducing the possibility of failure by screws 58 or 59. Angulation portion 40 is discussed in further detail in conjunction with FIG. 5.

HTO device 10 may be manufactured using a variety of materials with suitable tensile properties such as, but not limited to, steel or a polymeric plastic. That is, HTO device 10 may utilize materials suitable to withstand the stresses that may be associated with compression and selective adjustment during treatment of the patient.

In operation, HTO device 10 may be used for a period of time suitable for healing. A physician may provide a treatment plan that includes continuous treatment or treatment at various intervals. For example, a patient may be instructed to adjust HTO device 10 by operating hex socket 42 in small increments, a number of times daily. Hex socket 42 is proximally disposed and easy for a patient to operate by rotating either clockwise or counterclockwise. Such an advantage also provides immediate angulation of osteotomy 132, thus reducing the effective treatment period required. That is, the patient need not wait for a lengthening or distraction period to be completed before angulation begins, as with most conventional anteriorly-placed HTO devices 10.

It may be particularly advantageous for the patient to rotate hex socket 42 one-quarter turn four times per day. This schedule may provide approximately one millimeter (1 mm) of adjustment per day. Such an advantage may prevent or reduce the risk of bone consolidation or solidification, while allowing bone regeneration. This may also permit full desired angulation to be achieved. The treatment plan may be changed over the course of healing, and may vary from patient to patient. For example, those patients who are younger and/or healthier may increase the amount of rotation and/or the daily repetition thereof.

The patient may adjust HTO device 10 to enlarge distance D and length L in accordance with the treatment plan. Such enlargement provides valgus and/or varus correction by angulating bone 122 as proximal pins 22 are separated further from distal pins 22. For example, the physician may determine that valgus and/or varus correction requires extension of distance D to a new distance D', and/or adjustment of adjustment angle θ to a new angle θ'. One example for such an extension is discussed in further detail in conjunction with FIG. 4.

Figure 4:
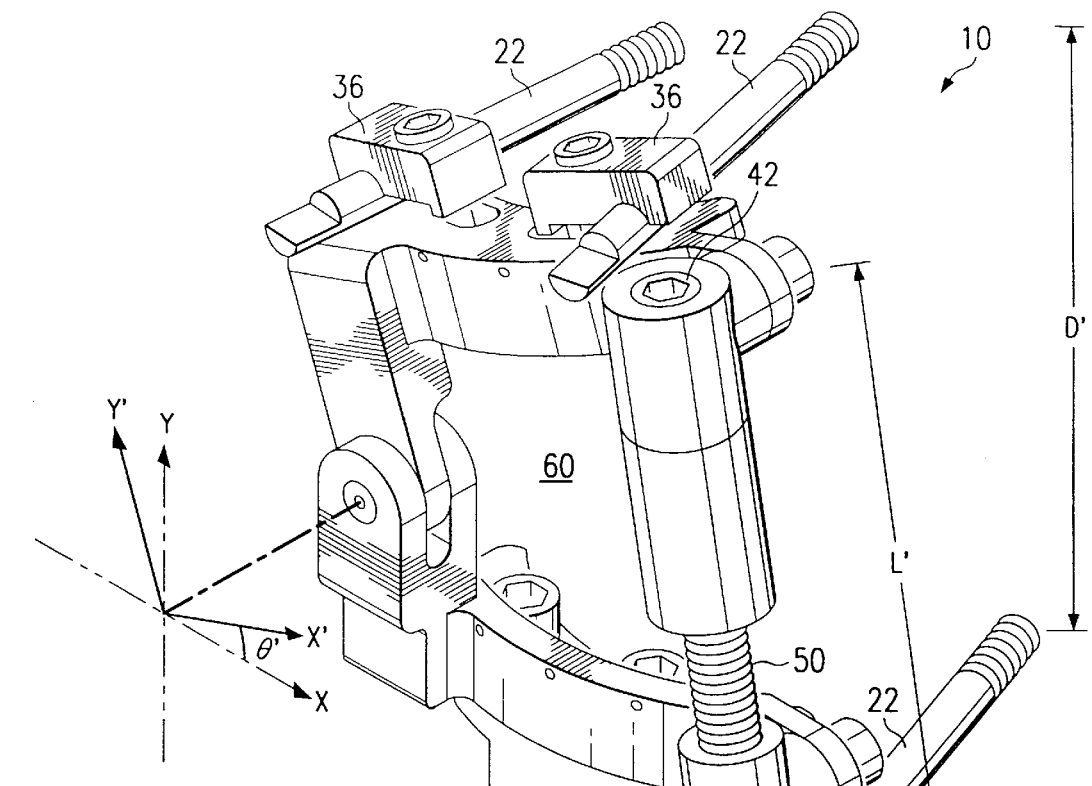
FIG. 4 is a schematic drawing showing an isometric view of a high tibial osteotomy device with an extended window incorporating the teachings of the present invention.

FIG. 4 is a schematic drawing showing an isometric view of a high tibial osteotomy device with an extended window incorporating the teachings of the present invention. Distance D between proximal pins 22 and distal pins 22 (as illustrated in FIG. 1) has been extended to a new distance D'. In addition, length L of adjustment portion 40 (as illustrated in FIG. 1) has been extended to a new length L'. In this embodiment, threaded rod 50 has been rotated by operating hex socket 42 to separate upper cap 44 from body 48. Rotation of threaded rod 50 rotates adjustment θ about the axis of rotation at hinge 28. Adjustment angle θ (as discussed in FIG. 1) has increased to an angle θ' that is between 0.0 degrees and 90.0 degrees.

Window 60 has also been enlarged by adjustment of adjustment portion 40. A variety of techniques may be used to accommodate an increase and/or decrease in adjustment angle θ as length L is increased. For example, proximal and distal pins 22 maintain positioning of HTO device 10 in tibial bone 122. In addition, in this embodiment, adjustment portion 40 slightly rotates relative to first portion 24 and second portion 26. Upper screw 58 and lower screw 59 allow slight rotation of adjustment portion 40 relative to first portion 24 and second portion 26, respectively.

Figure 5:
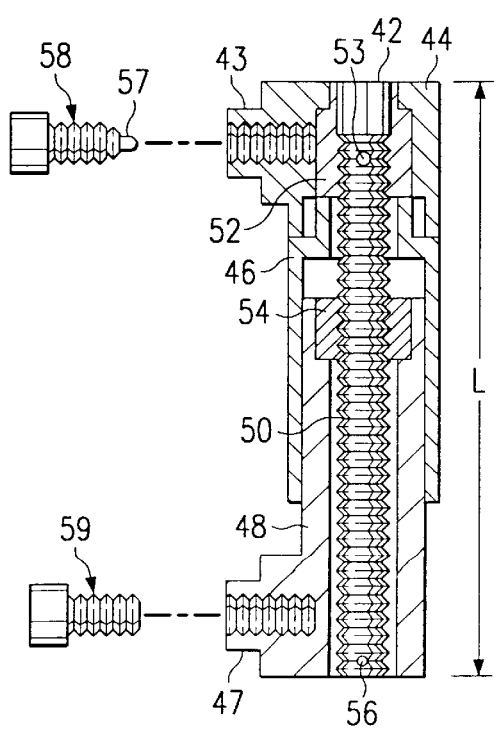
FIG. 5 is a schematic drawing illustrating a cross-sectional view of an adjustment portion of the high tibial osteotomy illustrated in FIG. 3.

FIG. 5 is a schematic drawing illustrating a cross-sectional view of an adjustment portion of the high tibial osteotomy illustrated in FIG. 3. The invention contemplates a variety of configurations for adjustment portion 40. For example, adjustment portion 40 includes hex socket 42 which is rigidly connected to a threaded rod 50. In operation, as a patient rotates hex socket 42, threaded rod 50 rotates and lifts hex socket 42 a distance from body 48. Threaded rod 48 may in some applications be a lifting rod that is manufactured to provide lifting capability.

In this embodiment, adjustment portion 40 includes upper cap 44, barrel 46, and body 48. Threaded rod 50 is also rigidly connected by, for example, pin 53, to a socket-containing member 52 which rotates within cap 44. A nut 54 is rigidly connected to body 48. Adjustment portion 40 may also include a means to stop or limit the distance that threaded rod 50 may be moved relative to body 48. For example, it may be desirable in some applications for threaded rod 50 to include a pin 56 that protrudes from threaded rod 50. This pin may travel in the threads of body 48 and stop the movement of threaded rod 50 through nut 54. Other methods and devices may be used to rigidly connect various components including, but not limited to, gluing and/or welding techniques.

In some embodiments, it may also be desirable to reduce or prevent slippage of threaded rod 50. For example, socket-containing member 52 may include one or more grooves (not explicitly shown) disposed in a direction generally parallel to length L. These grooves may extend the entire length of socket-containing member 52, or some portion thereof. A ball plunger assembly 57 may be used in conjunction with these grooves. For example, ball plunger assembly 57 includes a threaded rod in which a ball or other protrusion resides. When a patient rotates hex socket 42, threaded rod 50 and socket-containing member 52 may move relative to ball plunger assembly 57, depressing the ball or protrusion into the groove of socket-containing member 52. When the next groove is reached, the ball protrudes from the threaded rod into the groove, effectively limiting movement of threaded rod 50 by means of friction. In one embodiment of the invention and as illustrated in FIG. 5, ball plunger assembly 57 may be disposed within upper screw 58 that has been adapted to receive the threaded rod.

In some embodiments, it may also be desirable to provide a patient with tactile and/or audible feedback as the patient operates hex socket 42. As one example, ball plunger assembly 57 may be used to provide such feedback. It may be desirable for the grooves to be disposed in socket-containing member 52 at ninety-degree intervals. Such a configuration may allow tactile and/or audio feedback when threaded rod 50 is rotated in a one-quarter turn increment. For example, as the ball protrudes into the groove, it may make an audible click that may be used to signal the patient that one-quarter turn of hex socket 42 has been achieved. In some applications, it may be desirable to use a ball plunger assembly 57 with a ball whose diameter is one-quarter the diameter of threaded rod 50.

The present invention may be utilized for both the right and left limbs for both medial and lateral osteotomies. That is, angulation portion 20 may be used in conjunction with stabilizing portion 70 to control final limb alignment and apply gradual correction angulation means to either tibia 122. Such an advantage may desirably improve the interchangeability of elements for HTO device 10 and may reduce manufacturing costs. In the embodiment illustrated in FIGS. 1–4, HTO device 10 may be used in the correction of a laterally-positioned transverse osteotomy 132 on a left tibia 122.

HTO device 10 may be operated in similar fashion for a medially-positioned or laterally-positioned osteotomy 132 for either leg. For example, angulation portion 70 may be controlled on either side of the patient's leg by appropriately reversing the center of rotation. To reverse the center of rotation, angulation portion 20 may be rotated and selected elements may be releasably coupled thereto in an alternative configuration. For example, stabilizing portion 70 may be coupled to first portion 24, rather than second portion 26, of angulation portion 20. Thus, in this embodiment, second portion 26 would be proximally located and first portion 24 would be distally located.

Support member 79 may then be coupled to slot 31 of first portion 24, rather than second portion 26, of angulation portion 20. Clamp mechanisms 36 may also be coupled to slot 81 of second portion 26, rather than first portion 24, of angulation portion 20 so that they are once again proximally located. Similarly, clamp mechanisms 76A and 76B may be releasably coupled to side 84 of stabilizing portion 70. Clamp mechanisms 36, 76A and 76B may also be similarly selectively adjusted so that pins 22 may be appropriately positioned, as discussed in conjunction with FIGS. 1–3.

In addition, adjustment portion 40 may also be flipped to proximally locate hex socket 42. That is, cap 44 would be coupled to second portion 26, and body 48 would be coupled to first portion 24. A screw 58 including a ball plunger assembly may also be used to couple cap 44 to second portion 26, if desired.

Figure 6:
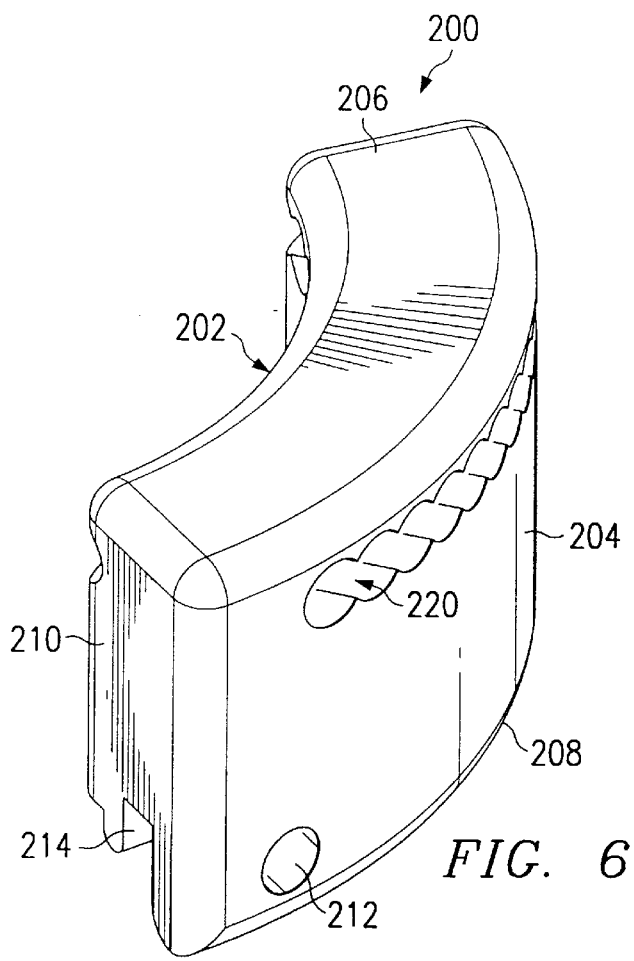
FIG. 6 is a schematic drawing showing an isometric view of an osteotomy guide incorporating teachings of the present invention.
Figure 8:
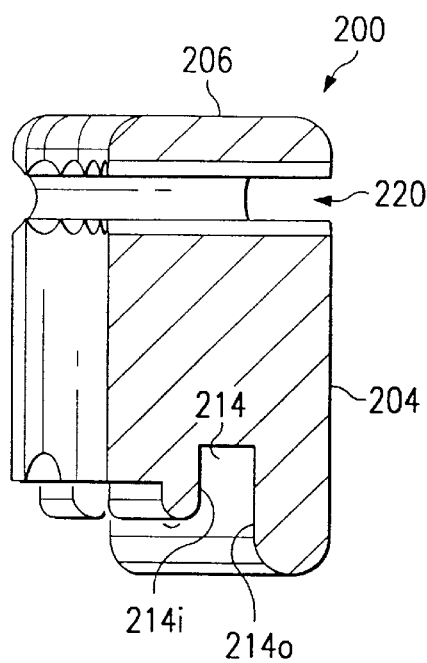
FIG. 8 is a schematic drawing illustrating a cross-sectional view of the osteotomy guide of FIG. 7.
Figure 7:
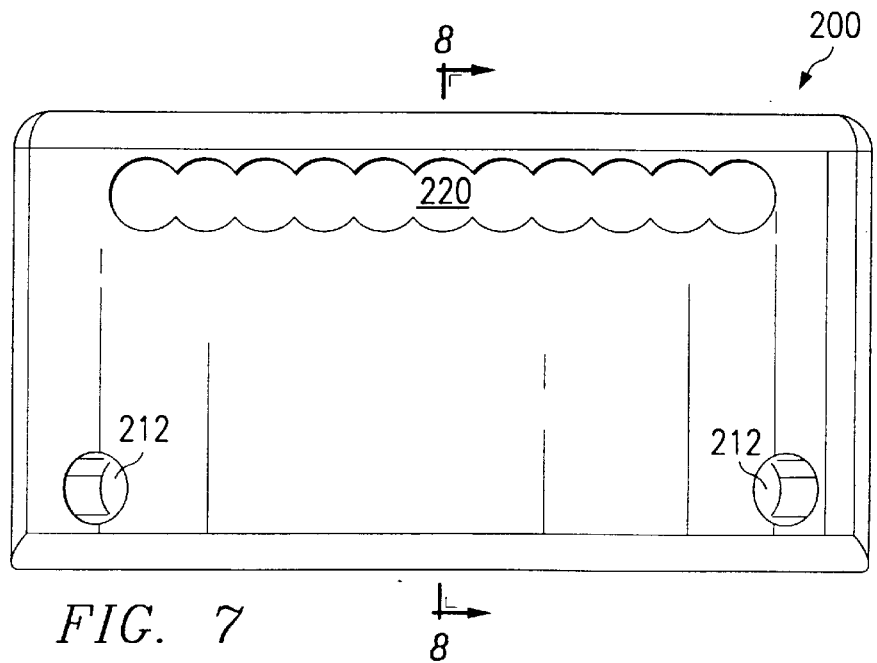
FIG. 7 is a schematic drawing showing a front view of the osteotomy guide of FIG. 6.

FIGS. 6–8 illustrate an example of an embodiment for an osteotomy guide. Osteotomy guide 200 may be used by a physician to create an osteotomy 132, and to improve the accuracy of tibial angulation by aligning osteotomy 132 with the center of rotation for HTO device 10. For example, osteotomy 132 may be created in tibia 122 at a location generally even with hinge 28. Such alignment may improve the angulation of tibia 122 and control thereof. Osteotomy guide 200 may desirably be removably inserted between first portion 24 and second portion 26 to perform an osteomatic procedure. After the procedure is complete, the physician may remove and discard osteotomy guide 200.

FIG. 6 is a schematic drawing showing an isometric view of an osteotomy guide incorporating teachings of the present invention. Osteotomy guide 200 preferably includes an inner surface 202, an outer surface 204, first surface 206, second surface 208, and two edges 210. Osteotomy guide 200 also preferably includes receptacle 220, which may be generally parallel with first and second surfaces 206 and 208. Osteotomy guide 200 also preferably includes two receptacles 212. In some applications, osteotomy guide 200 may reside in a volume whose surface is generally contoured to that of HTO device 10. In this embodiment, inner surface 202 and outer surface 202 is generally concavely shaped relative to tibia 122.

Osteotomy guide 200 may be formed from any semi-rigid material including, but not limited to, polycarbonate, aluminum, stainless steel, and/or acrylic. In some applications, osteotomy guide 200 may desirably be transparent or clear. Use of such materials may improve a physician's ability to view and/or control the osteotomy procedure.

FIG. 7 is a schematic drawing showing a front view of the osteotomy guide of FIG. 6. FIG. 7 illustrates a scalloped and generally linear receptacle 220 that is generally parallel to first surface 206 and second surface 208. The present invention also contemplates the use of other orientations and/or shapes for receptacle 220 such as an arc shape.

Receptacle 220 is desirably disposed at a location within osteotomy guide 200 to align with hinge 28 of HTO device 10. In the embodiment shown, receptacle 220 is disposed nearer to first surface 206 than to second surface 208. Such a configuration also provides a separation between receptacle 220 and HTO device 10 suitable for tools such as a drill. In this embodiment, receptacle 220 includes a plurality of generally circular receptacles that are each adapted to receive a drill bit. This plurality of circular shaped receptacles may be equally spaced from center to center, and may facilitate creation of a generally linear osteotomy that comprises a series of holes that are drilled into tibia 122. An osteotome or chisel may be used to further separate the bone tissue between the drilled holes, completing the osteotomy 132. The present invention contemplates a variety of sizes for any number of receptacles. For example, receptacle 220 may include eleven drill receptacles each approximately six millimeters (6 mm) in diameter, spaced approximately 4.8 mm from center to center. The present invention also contemplates a variety of receptacles 220 through which a variety of cutting mechanisms such as saw blades may penetrate to form osteotomy 132.

FIG. 8 is a schematic drawing illustrating a cross-sectional view of the osteotomy guide of FIG. 7. Osteotomy guide 200 may be releasably coupled to HTO device 10 using a variety of methods. In this embodiment, osteotomy guide 200 may be snugly coupled to HTO device 10 by means of a screw (not explicitly shown).

By way of example and not by limitation, osteotomy guide 200 comprises a generally U-shaped notch 214 that generally forms to surfaces 62 or 64 of second portion 26. As illustrated, notch 214 includes an inner portion 214a that is shorter than an outer portion 214b. Osteotomy guide 200 may be releasably coupled to HTO device 10 by placing notch 214 over surfaces 62 or 64. For example, osteotomy guide 200 may be translated along surface 62 until a desirable position has been reached. Then, screws (not explicitly shown) may be inserted through receptacles 212 to penetrate portion 214b and snugly couple second portion 26 to inner portion 214a. After the osteotomical procedure has been performed, the physician may unscrew osteotomy guide 200 from HTO device 10 and/or discard osteotomy guide 200.

Although the present invention and its advantages have been described in detail it should be understood that various changes, substitutions, and alterations can be made hereto without departing from the spirit and scope of the invention as defined by the following claims.

What is claimed is:

1. The apparatus of claim 1, wherein the angulation portion comprises a window formed by:
   a second portion coupled to the stabilizing portion;
   a first portion adapted to connect to the patient's bone and hingedly coupled to the second portion at the axis of rotation; and
   an adjustment portion rotatably coupled to the stabilizing and angulation portions.

2. The apparatus of claim 1, wherein the adjustment portion comprises a threaded rod.

3. The apparatus of claim 2, further comprising the angulation portion selectively adjustable through audio feedback.

4. The apparatus of claim 2, further comprising the angulation portion selectively adjustable through tactile feedback.

5. The apparatus of claim 2, further comprising the angulation portion selectively adjustable in increments by the patient.

6. The apparatus of claim 2, further comprising at least one of the group consisting of the stabilizing portion and the angulation portion selectively adjustable to compress an osteotomy.

7. The apparatus of claim 2, further comprising the angulation portion releasably coupled to the stabilizing portion.

8. The apparatus of claim 2, further comprising the angulation portion and the stabilizing portion operable for attachment with either a left tibial bone or a right tibial bone.

9. The apparatus of claim 2, further comprising the angulation portion manufactured using polymeric plastic materials.

10. The apparatus of claim 9, further comprising a window formed by:

a second portion coupled to the stabilizing portion; and a first portion adapted to connect to the tibial bone and hingedly coupled to the second portion at the axis of rotation; and the adjustment portion rotatably coupled to the stabilizing and angulation portions.

11. The apparatus of claim 10, further comprising the adjustment portion selectively adjustable through at least one of audio feedback and tactile feedback.

12. The apparatus of claim 10, further comprising the adjustment portion selectively adjustable in increments by the patient.

* * * * *

UNITED STATES PATENT AND TRADEMARK OFFICE
CERTIFICATE OF CORRECTION

PATENT NO. : 6,423,061 B1
DATED : July 23, 2002
INVENTOR(S) : Richard M. Bryant

It is certified that error appears in the above-identified patent and that said Letters Patent is hereby corrected as shown below:

Column 10,
Beginning with line 55, please delete claims 1 through 12 in their entirety and replace with the allowed claims 1 through 12 as follows:

--1. An external fixation apparatus, the apparatus comprising:
a stabilizing portion adapted to be externally coupled to an anterior portion of a patient's bone;
an angulation portion adapted to be externally coupled to another anterior portion of the patient's bone and coupled to the stabilizing portion;
the angulation portion selectively adjustable to angulate a portion of the patient's bone about an axis of rotation offset from a longitudinal axis of the patient's bone;
the angulation portion including a window formed by a second portion coupled to the stabilizing portion;
a first portion adapted to connect to the patient's bone and hingedly coupled to the second portion at the axis of rotation; and
an adjustment portion rotatably coupled to the stabilizing and angulation portions.

2. The apparatus of claim 1, wherein the adjustment portion comprises a threaded rod.

3. The apparatus of claim 2, further comprising the angulation portion selectively adjustable through audio feedback.

4. The apparatus of claim 2, further comprising the angulation portion selectively adjustable through tactile feedback.

5. The apparatus of claim 2, further comprising the angulation portion selectively adjustable in increments by the patient.

6. The apparatus of claim 2, further comprising at least one of the group consisting of the stabilizing portion and the angulation portion selectively adjustable to compress an osteotomy.

7. The apparatus of claim 2, further comprising the angulation portion releasably coupled to the stabilizing portion.

UNITED STATES PATENT AND TRADEMARK OFFICE
CERTIFICATE OF CORRECTION

PATENT NO.    : 6,423,061 B1
DATED         : July 23, 2002
INVENTOR(S)   : Richard M. Bryant It is certified that error appears in the above-identified patent and that said Letters Patent is hereby corrected as shown below:

Column 10 (cont'd),

8. The apparatus of claim 2, further comprising the angulation portion and the stabilizing portion operable for attachment with either a left tibial bone or a right tibial bone.

9. The apparatus of claim 2, further comprising the angulation portion manufactured using polymeric plastic materials.

10. A high tibial osteotomy apparatus, the apparatus comprising:
a stabilizing portion adapted to be externally coupled to an anterior portion of a tibial bone;
an angulation portion coupled to the stabilizing portion;
an adjustment portion coupled to the angulation portion;
the angulation portion adapted to be externally coupled to another anterior portion of the tibial bone;
the angulation portion operable to angulate a portion of the tibial bone about an axis of rotation offset from a longitudinal axis of the tibial bone following an osteotomical procedure on the tibial bone;
a window formed by a second portion coupled to the stabilizing portion;
a first portion adapted to connect to the tibial bone and hingedly coupled to the second portion at the axis of rotation; and
the adjustment portion rotatably coupled to the stabilizing and angulation portions.

11. The apparatus of claim 10, further comprising the adjustment portion selectively adjustable through at least one of audio feedback and tactile feedback.

12. The apparatus of claim 10, further comprising the adjustment portion selectively adjustable in increments by the patient.--

Signed and Sealed this

Ninth Day of March, 2004

JON W. DUDAS
*Acting Director of the United States Patent and Trademark Office*